(12) United States Patent
Bonsignore et al.

(10) Patent No.: US 8,262,720 B2
(45) Date of Patent: Sep. 11, 2012

(54) PROSTHESIS COMPRISING DUAL TAPERED STENT

(75) Inventors: Craig Bonsignore, San Jose, CA (US); Tom Duerig, Fremont, CA (US); Gregory Mast, Fremont, CA (US)

(73) Assignee: Nitinol Development Corporation

( * ) Notice: Subject to any disclaimer, the term of this patent is extended or adjusted under 35 U.S.C. 154(b) by 294 days.

(21) Appl. No.: 11/001,813

(22) Filed: Dec. 2, 2004

(65) Prior Publication Data
US 2006/0122685 A1    Jun. 8, 2006

(51) Int. Cl.
*A61F 2/86* (2006.01)
(52) U.S. Cl. ............ 623/1.13; 623/1.15; 623/1.34
(58) Field of Classification Search ............ 623/1.13, 623/1.15, 1.3, 1.31, 1.18
See application file for complete search history.

(56) References Cited

U.S. PATENT DOCUMENTS

| | | | | |
|---|---|---|---|---|
| 4,733,665 A * | 3/1988 | Palmaz | ............ | 606/108 |
| 5,102,417 A * | 4/1992 | Palmaz | ............ | 606/195 |
| 5,395,390 A * | 3/1995 | Simon et al. | ............ | 623/1.18 |
| 5,449,373 A * | 9/1995 | Pinchasik et al. | ............ | 606/198 |
| 5,690,667 A * | 11/1997 | Gia | ............ | 606/191 |
| 5,800,514 A | 9/1998 | Nunez et al. | ............ | 623/1.51 |
| 6,053,941 A * | 4/2000 | Lindenberg et al. | ............ | 606/108 |
| 6,110,198 A * | 8/2000 | Fogarty et al. | ............ | 623/1.12 |
| 6,241,762 B1 * | 6/2001 | Shanley | ............ | 623/1.17 |
| 6,273,910 B1 * | 8/2001 | Limon | ............ | 623/1.15 |
| 6,485,509 B2 * | 11/2002 | Killion et al. | ............ | 623/1.15 |
| 6,533,810 B2 * | 3/2003 | Hankh et al. | ............ | 623/1.16 |
| 6,579,314 B1 * | 6/2003 | Lombardi et al. | ............ | 623/1.44 |
| 6,592,615 B1 | 7/2003 | Marcade et al. | ............ | 623/1.16 |
| 6,596,023 B1 * | 7/2003 | Nunez et al. | ............ | 623/1.3 |
| 2002/0147492 A1 * | 10/2002 | Shokoohi et al. | ............ | 623/1.13 |
| 2002/0156523 A1 * | 10/2002 | Lau et al. | ............ | 623/1.13 |
| 2003/0040803 A1 | 2/2003 | Rioux et al. | ............ | 623/23.7 |
| 2004/0082990 A1 | 4/2004 | Hartley | ............ | 623/1.13 |

FOREIGN PATENT DOCUMENTS

| | | |
|---|---|---|
| EP | 0686379 B1 | 12/1995 |
| EP | 0 938 879 A2 | 9/1999 |
| EP | 0 938 879 A3 | 9/1999 |
| EP | 1 044 663 A2 | 10/2000 |
| EP | 1 044 663 A3 | 10/2000 |

OTHER PUBLICATIONS

European Search Report EP 05257247.6 dated Mar. 31, 2006.
International Office Action for related Application No. CA 2,528,717 dated Jun. 22, 2009. International Office Action for related Application No. CA 2,528,717 dated Feb. 5, 2010.
International Office Action for related Application No. EP 05 257 247.6 dated Dec. 18, 2009.
European Exam Report dated Dec. 28, 2011 in corresponding European Patent Application No. 05257247.6.

* cited by examiner

*Primary Examiner* — Ryan Severson

(57) ABSTRACT

The present invention is directed to a prosthesis for treating, repairing and/or replacing an abdominal aortic aneurysm. The prosthesis includes a stent having a first end and a second end with an intermediate section therebetween. The first end and seconds ends each include an anchor, wherein one or both anchor(s) has a diameter that is larger than the diameter of the intermediate section. The prosthesis also comprises graft material engaging at least a portion of the stent. The present invention is also directed to a prosthesis for repairing an aneurysm comprising a stent having a first end and a second wend with an intermediate section disposed therebetween. The first and second ends each include means for sealing the respective ends to a structure, wherein the intermediate section has a diameter that is smaller than the diameter of the first or second end. Graft material engages at least a portion of the stent.

6 Claims, 1 Drawing Sheet

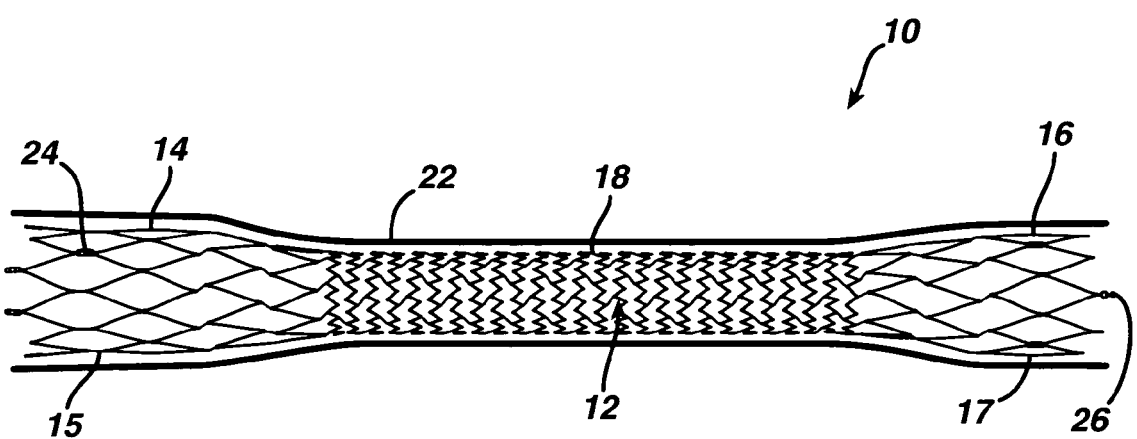

PROSTHESIS COMPRISING DUAL TAPERED STENT

BACKGROUND OF THE INVENTION

1. Field of the Invention

The present invention relates to devices and methods for repairing aneurysms. More particularly, the present invention relates to a prosthesis comprising a dual tapered stent.

2. Discussion of the Related Art

An endoprosthesis or stent-graft is commonly used as a tubular structure left inside the lumen of a duct to relieve an obstruction. Commonly, endoprostheses are inserted into the lumen in a non-expanded form and are then expanded autonomously or with the aid of a second device in situ. The endoprosthesis may be self-expanding, or expansion may occur through the use of a catheter mounted angioplasty balloon, in order to shear and disrupt the obstructions associated with the wall components of the vessel and to obtain an enlarged lumen. In the absence of an endoprosthesis, restenosis may occur as a result of elastic recoil of the stenotic lesion.

The endoprosthesis should preferably be of a somewhat rigid design to provide reinforcement support and may be required to be of considerable length in order to extend over a lengthy diseased area. It is difficult to resolve this need for rigidity with the need of having a flexible endoprosthesis which is readily implanted by inserting it through a sometimes tortuous curving path as is often encountered in a percutaneous insertion technique typically used for implantation of endoprosthesis. This is further complicated by the fact that the endoprosthesis must be readily expandable upon implantation to provide support structure.

Although a number of stent designs for use in endoprostheses have been reported, these designs have suffered from a number of limitations. These include restrictions on the dimensions and flexibility of the stent. For example, a stent having rigid ends and a flexible median part is typically formed of multiple parts and is not continuously flexible along the longitudinal axis. Other stents exist that are longitudinally flexible but consist of a plurality of cylindrical elements connected by flexible members. This design has at least one important disadvantage. For example, according to this design, protruding edges occur when the stent is flexed around a curve raising the possibility of inadvertent retention of the stent on plaque deposited on arterial walls. This may cause the stent or plaque to embolize or move out of position and further cause damage to the interior lining of healthy vessels.

SUMMARY OF THE INVENTION

The flexible prosthesis of the present invention overcomes the limitations of the devices and methods as briefly described above.

The present invention is directed to a prosthesis comprising a stent having a first end and a second end with an intermediate section therebetween. The first and second ends each include an anchor, wherein at least one anchor has a diameter that is larger than the diameter of the intermediate section. The prosthesis also comprises graft material engaging at least a portion of the stent.

More particularly, the stent is comprised of shape memory material and the intermediate section is flexible. The diameter of the first end and the diameter of the second end of the stent is preferably between about 15 mm and about 25 mm. The diameter of the intermediate section of the stent is preferably between about 8 mm and about 12 mm. The first end of the stent is configured to attach to another device within a lumen such as a prosthesis, stent, or stent gasket, and the second end of the stent is configured to be anchored within the interior wall of a lumen.

Another aspect of the present invention is directed to a prosthesis for repairing an aneurysm. The prosthesis comprises a stent having a first end and a second end with an intermediate section disposed therebetween. The first end and the second end each include a means for sealing the respective end to a structure. The first and/or second end each has a diameter that is larger than the diameter of the intermediate section. The prosthesis also comprises graft material engaging at least a portion of the stent.

More particularly, the first end of the stent is configured to form a seal with another device within a lumen, such as a prosthesis, stent, or stent gasket, and the second end is configured to form a seal with the interior wall of the lumen.

The present invention is also related to a method for repairing an abdominal aortic aneurysm comprising delivering a prosthesis within an interior wall of a lumen. The prosthesis comprises a stent having a first end and a second end with an intermediate section therebetween. The first and/or second ends of the stent each have a diameter larger than the diameter of the intermediate section of the stent. The prosthesis also comprises graft material engaging at least a portion of the stent.

More particularly, the stent is comprised of shape memory material. Furthermore, the first end of the stent is attached to another device within the lumen, and the second end of the stent is anchored within the interior wall of the lumen. The prosthesis may provide a conduit for fluid flow to the iliac artery.

The accompanying FIGURE shows an illustrative embodiment of the invention from which these and other of the objectives, novel features and advantages will be readily apparent.

BRIEF DESCRIPTION OF THE DRAWINGS

FIG. 1 is a side view of a prosthesis in accordance with the present invention.

DETAILED DESCRIPTION OF THE PREFERRED EMBODIMENTS

Definitions

As used herein, aortic aneurysm refers to any failure of a conduit, such as an aortic wall, typically characterized by an undesirable dilation of a portion of the artery, vessel malformation, or an occlusion. The methods and structures of the present invention may be used to treat, repair, replace, or bypass any blood vessel (e.g., artery, vein, capillary); any fluid carrying vessel (e.g., lymphatic vessels); any organ or portion thereof that includes a blood or fluid vessel; or any junction between blood vessels, between fluid vessels, and between organs and blood vessels. An exemplary use of methods and structures of the present invention is to repair an aortic aneurysm, and the use of such term is not intended to limit the use of the methods or structures of the present invention to repair or replace other conduit failures. The structures and methods of the present invention may also be utilized in the thoracic aorta, and may be used to repair thoracic aneurysms or thoracic dissecting aneurysms. Accordingly, use of the term "aortic aneurysm" is intended to relate to and include other aneurysms, including but not limited to both abdominal aortic aneurysms and thoracic aneurysms.

In preferred embodiments of the invention, the methods and structures are used to treat, repair, replace, or bypass an abdominal aortic aneurysm. As used herein fluid pathway refers to any in vivo structure through which a biological fluid passes. A preferred fluid pathway is an artery. Fluid pathways include, but are not limited to channels formed by an artery a vein, a capillary, lymph nodes and channels, and arteries, veins, and capillaries within an organ or organelle.

As used herein fluid or biological fluid refers to any fluid produced by an animal, including a human. Exemplary biological fluids include, but are not limited to blood, oxygenated blood, de-oxygenated blood, gastric fluids, amniotic fluid, spinal fluid, and lymph. The preferred fluid is blood or oxygenated blood.

As used herein, adapted for communication, communicating, or similar terms refer to any means, structures, or methods for establishing operational association between two elements of the system. Similarly, engaging, adapted to engage, or similar terms refer to means, structures, or methods for contacting a first component, structure, or portion thereof with a second component, structure, or portion thereof. Exemplary structures are shown in the Figure. Typically, all of these terms and phrases refer to at least one structure in or on a first component configured to engage a complementary structure in or on a second component, and the use of these inter-engaging features to link a first component with a second component. The engagement or communication may be matingly for example, permanent and/or releasably, for example, temporary. In preferred embodiments of the invention, communication or engagement may be fluid tight, substantially fluid tight, or fluid tight to an extent so as to not substantially compromise the intended function of the structure.

For example, a connector may be adapted to receive or connect to a complementary connector on another graft or prosthesis. As used herein, connector refers to any structure used to form a joint or to join itself to another component or portion thereof. These connectors or connections establish a fluid flow path through various elements of the apparatus, assembly, or system. In a preferred embodiment of the invention, the methods or structures are intended to establish at least one fluid flow path through a vessel, conduit, organ, or portions thereof. Typical connections include but are not limited to mating connections, such as Luer-type, screw-type, friction-type, or connectors that are bonded together.

As used herein, distal is used in accordance with its ordinary dictionary definition, i.e., referring to a position farthest from the beginning; in human anatomy, this term is commonly equivalent to caudal or inferior. Proximal is used in accordance with its ordinary dictionary definition, i.e., referring to a position nearest the beginning; in human anatomy, this term is commonly equivalent to cranial or superior. The terms distal and proximal are intended to convey opposite ends or portions of a device, channel, element, or structure.

In relation to a fluid flow path, distal will typically refer to a downstream location in the fluid flow path, and proximal will typically refer to an upstream location, unless otherwise specifically noted. Anatomically, distal generally refers to "away from the heart" and proximal generally refers to "toward the heart."

The apparatuses and methods of the present invention may be used in the treatment of aortic aneurysms, preferably an abdominal aortic aneurysm, among other uses noted below. A better understanding of the present device and its use in treating aortic aneurysms will be achieved by reading the following description in conjunction with the following incorporated references.

Referring to FIG. 1, there is shown a prosthesis 10 comprising a stent 12 defining an interior space or lumen having an open first end 14 comprising an anchor 15, and an open second end 16 comprising an anchor 17, with an intermediate section 18 therebetween. As illustrated, the diameter of the first end 14 and the diameter of the second end 16 of the stent 12 are larger than the diameter of the intermediate section 18. However, in alternate exemplary embodiments, only one of the two ends may have a larger diameter. Preferably, the diameter of the first end 14 and the diameter of the second end 16 are each between about 15 mm and about 25 mm. The diameter of the intermediate section 18 of the stent 12 is preferably between about 8 mm and about 12 mm.

The stent 12 may be comprised of any material suitable for functioning in vivo and which allows for a variation in diameter along the length of the stent. Preferably, the stent 12 is comprised of shape memory material. The shape memory material may be comprised of various materials including, but not limited to shape memory metals or metal alloys. Preferably, the shape memory material is comprised of a Nickel Titanium alloy (Nitinol).

In preferred embodiments of the invention, the stent material and prosthesis 10 are expandable or collapsible, i.e., moveable from a first closed position to a second open position, or vice versa. The stent 12 and prosthesis 10 of the present invention may also be self-expandable.

The stent 12, may comprise an expandable lattice or network of interconnected struts. In preferred embodiments of the invention, the lattice is fabricated, e.g., laser cut, from an integral tube of material. It is preferred that the stent 12 structure be continuous and extend the full length of the stent, rather than consist of a series of individual support structures attached via sutures or some other mechanism to graft material. It is also preferred that the intermediate section 18 of the stent 12 be comprised of periodically joined, substantially zig-zag shaped struts in order to increase flexibility of the intermediate section. In addition, the first end 14 and the second end 16 of the stent 12 are each preferably comprised of substantially diamond shaped struts to increase radial strength and anchor stability of the ends.

The design of the stent 12 and prosthesis 10 of the present invention combines the necessity of large diameter ends 14 and 16 for anchoring and/or sealing means within a lumen, with the advantage of a reduced diameter body or intermediate section 18. The first and second ends 14 and 16 of the stent 12 may be strong and stiff to provide a sufficient anchor and seal within a lumen. The intermediate section 18 of the stent 12 has a reduced diameter which provides strength and flexibility to the stent and prosthesis 10, allowing them to be contoured with ease and conform to accommodate varying anatomy. The intermediate section 18 of the stent provides an uncompromised conduit for flow within a lumen without kinking.

The stent 12 of the present invention forms a support or lattice structure suitable for supporting a graft material 22. The stent 12 of the present invention maintains lumen patency in the prosthesis 10 while maintaining flexibility and kink resistance by using a design having two ends 14 and 16 which taper to a reduced diameter body or intermediate section 18. In preferred embodiments of the present invention, the stent 12 defines a channel through which a fluid, such as blood, may flow. For example, the prosthesis 10 of the present invention may be used to repair an abdominal aortic aneurysm by delivering the prosthesis within the interior wall of a lumen.

The stent 12, including the first end 14, second end 16 and intermediate section 18, is preferably covered with a continuous graft material 22 which also varies in diameter along its length, whereby the ends of the graft material have a larger diameter than the intermediate section of the graft material, as illustrated in FIG. 1. The stent 12 may be designed to match the diameter of the expanded graft material 22. Alternately, the stent 12 may be designed to be larger than the expanded graft material 22, in which case the graft material 22 will constrain the stent 12 and dictate the diameter of the stent 12 and prosthesis 10.

The graft material 22 may be made from any number of materials known to those having skill in the art, including but not limited to woven polyester, Dacron®, Teflon®, polyurethane, porous polyurethane, silicon, polyethylene terephthlate, expaned polytetrafluoroethylene (ePTFE) and blends of various materials.

In some exemplary embodiments of the present invention, it may be desirable to incorporate a biodegradable, or degradable material, such as albumin, or a collagen. A graft material 22 that is biodegradable would erode or dissolve over time; however it is believed that a layer of endothelium may grow as the graft material erodes. It is further believed that these new layers of endothelium may provide a new, fluid impervious lining within the aneurysm.

It is preferred that all of the foregoing materials be porous to allow for an intimal layer to form a biofusion structure or matrix.

The graft material 22 may be variously configured, preferably to achieve predetermined mechanical properties. For example, the graft material 22 may incorporate a single or multiple weaving and/or pleating patterns, or may be pleated or unpleated. For example, the graft 22 may be configured into a plain weave, a satin weave, include longitudinal pleats, interrupted pleats, annular or helical pleats, radially oriented pleats, or combinations thereof. Alternately, the graft material 22 may be knitted or braided. In the embodiments of the present invention in which the graft material 22 is pleated, the pleats may be continuous or discontinuous. Also, the pleats may be oriented longitudinally, circumferentially, or combinations thereof.

In accordance with the present invention, the graft material 22 may be impervious or substantially impervious to the flow of blood, or may be porous.

A graft material 22 is impervious if it prevents blood from passing through the graft material on contact with blood or after the graft material is saturated with blood. Choice of the flow characteristics of a graft material 22 are well known to those skilled in the art, and are tied in part to the intended function of the prosthesis 10 or portion of the prosthesis.

The foregoing graft material 22 may be knitted or woven, and may be warp or weft knitted. If the graft material 22 is warp knitted, it may be provided with a velour, or towel like surface; which is believed to speed the formation of blood clots, thereby promoting the integration of a prosthesis 10 or prosthesis component into the surrounding cellular structure.

In accordance with the present invention, it may be highly desirable to provide a graft material 22 that limits or eliminates the amount of blood that passes between the graft material and the arterial wall, to provide a catheter-delivered graft or prosthesis 10 that extends through a longer portion of an artery, to improve the anchoring and/or mechanisms between two prostheses, to improve the anchoring and/or sealing mechanism between the prosthesis 10 and the arterial wall or an interluminal cavity within an artery, and to improve the fluid dynamic and performance characteristics of the implanted prosthesis.

The stent 12 may be attached to the graft material 22 by any number of attachment means or methods known to those skilled in the art, including friction (if placed inside the graft); adhesives, such as polyurethane glue; a plurality of conventional sutures of polyvinylidene fluoride, polypropylene, Dacron®, or any other suitable material; ultrasonic welding; mechanical interference fit; loops; folds; sutures; and staples. For example, the stent 12 may also comprise attachment members 24. These attachment members 24 may be positioned at various locations around the stent 12 so that staples or sutures may be easily attached to the stent 12 for securing the graft material 22 thereto. These attachment members 24 would contain holes or eyelets for the staples or suturer. The attachment members 24 may also serve a dual purpose. In addition to connection points, the members 24 may also serve as radiopaque markers for facilitating prosthesis 10 placement. Alternately, they may just serve as markers. The stent 12 may be attached to the interior suface or exterior surface of the graft material 22 by any of the attachment means or methods described above.

The first end 14 of the stent 12 is typically the proximal or cranial end of the stent, and the second end 16 of the stent is typically the caudal or distal end. The first end 14 and second end 16 of the stent 12 may each be anchored within a lumen by anchoring the respective end directly to the interior wall of the lumen, or by attaching the first end 14 and/or second end 16 to another device within the lumen, such as to another stent, prosthesis or stent gasket. In a preferred embodiment, the cranial end 14 of the stent 12 is attached to and anchored within a stent gasket, or other prosthesis and the caudal end 16 is anchored directly to the interior wall of a lumen. In such an embodiment, the caudal end 16 of the stent 12 may be anchored within an iliac artery, for example, wherein the prosthesis 10 provides a closed conduit for blood flow from the stent gasket to the iliac artery. Also, the first end 14 and second end 16, when expanded, may each form a seal to a structure, e.g., to another stent, to a prosthesis, to a stent gasket, or to the interior wall of a lumen such as an iliac artery, as described above.

The stent 12 may also comprise one or more recapture legs 26 that extend from at least one of the two ends. The recapture legs 26 may comprise any suitable design that allows for the deployment device to recapture the deployed stent 12.

Specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A prosthesis for repairing an aneurysm comprising: a stent having a first end and a second end with an intermediate section disposed therebetween, the first and second ends having the same first pattern and the intermediate section having a second pattern different than the first pattern, the first and second ends including means for sealing the respective ends to a structure, the intermediate section having a diameter that is smaller than a diameter of the first or second end, the first and second ends being configured as fully closed diamond shaped elements for increased strength which taper from a first diameter to a second diameter, wherein the second diameter is less than the first diameter and equal to the intermediate section and the intermediate section being configured as a plurality of zig-zag shaped struts for increased flexibility joined by bridges, the bridges being connected in an angled manner to non-adjacent apexes of the zig-zags, the first and second ends being connected to the intermediate section by struts extending from the apexes of the diamond shaped elements and wherein the connection of the bridge on one set of zig-zag shaped struts is offset both longitudinally, circumferentially and having the opposite angular orientation from the connection on an adjacent set of zig-zag shaped struts, the stent being formed from a single laser cut tube; continuous graft material engaging substantially all of the stent, the continuous graft material being configured to match the diameter of the stent sections; and radiopaque attachment members for attaching the graft material to the stent.

2. The prosthesis of claim 1, wherein the stent is comprised of shape memory material.

3. The prosthesis of claim 1, wherein the diameter of the intermediate section is between about 8 mm and about 12 mm.

4. The prosthesis of claim 1, wherein the diameter of the first end and the diameter of the second end is between about 15 mm and about 25 mm.

5. The prosthesis of claim 1, wherein the first end is configured to form a seal with another prosthesis within a lumen, and wherein the second end is configured to form a seal with an interior wall of a lumen.

6. The prosthesis of claim 1, wherein the intermediate section is more flexible than the first and second ends.

* * * * *